United States Patent [19]

Ogilvie et al.

[11] Patent Number: 4,636,217
[45] Date of Patent: Jan. 13, 1987

[54] ANTERIOR SPINAL IMPLANT

[75] Inventors: James W. Ogilvie, Edina, Minn.; Frank R. Ogilvie, Leavenworth, Wash.

[73] Assignee: Regents of the University of Minnesota, Minneapolis, Minn.

[21] Appl. No.: 726,134

[22] Filed: Apr. 23, 1985

[51] Int. Cl.⁴ .............................................. A61F 2/44
[52] U.S. Cl. ..................................................... 623/17
[58] Field of Search ................. 623/17, 18; 128/69, 128/92 R, 42 B, 92 BB, 92 BC, 92 C

[56] References Cited

U.S. PATENT DOCUMENTS

| | | | |
|---|---|---|---|
| 3,867,728 | 2/1975 | Stubstad et al. | 3/1 |
| 4,085,744 | 4/1978 | Lewis et al. | 128/69 |
| 4,349,921 | 9/1982 | Kuntz | 3/1 |
| 4,361,141 | 11/1982 | Tanner | 128/69 |
| 4,401,112 | 8/1983 | Rezaian | 128/92 B |
| 4,422,451 | 12/1983 | Kalamchi | 128/69 |
| 4,433,677 | 2/1984 | Ulrich et al. | 128/69 |
| 4,502,473 | 3/1985 | Harris et al. | 128/92 A |
| 4,502,475 | 3/1985 | Weigle et al. | 128/92 EB |
| 4,502,483 | 3/1985 | Lacey | 128/303 R |
| 4,553,273 | 11/1985 | Wu | 128/92 C |
| 4,554,914 | 11/1985 | Kapp et al. | 623/17 |

OTHER PUBLICATIONS

Dunn, Harold K., M.D., *Instrumentation for the Anterior Spine*, 1984, University of Utah Medical Center, Salt Lake City, Utah.

Primary Examiner—Richard J. Apley
Assistant Examiner—James Prizant
Attorney, Agent, or Firm—Kinney & Lange

[57] ABSTRACT

A spinal implant prosthetic insert for implantation into a void in the spinal column in place of a diseased or injured vertebra that has been removed. The insert maintains the height of the anterior spinal column, thus preventing deformity from occurring. The prosthesis insert is implanted into the spinal column after the anterior vertebral body has been removed. The insert is rigidly fixed in place with bone screws that will screw into the adjacent upper and lower vertebrae after the insert has been positioned in place, through the operation of a drive that is accessible after the insert has been implanted into place. The insert is contoured so that no substantial part of it protrudes outside of the margins of the anterior vertebral column, making it usable as an implant even in the lumbar region where protrusions from the spinal column cannot be tolerated. The device is easily actuated after the anterior region of the spinal column has been exposed, and provides a rigidity that is limited only by the integrity of the bone of the adjacent vertebrae in which to is fixed.

13 Claims, 7 Drawing Figures

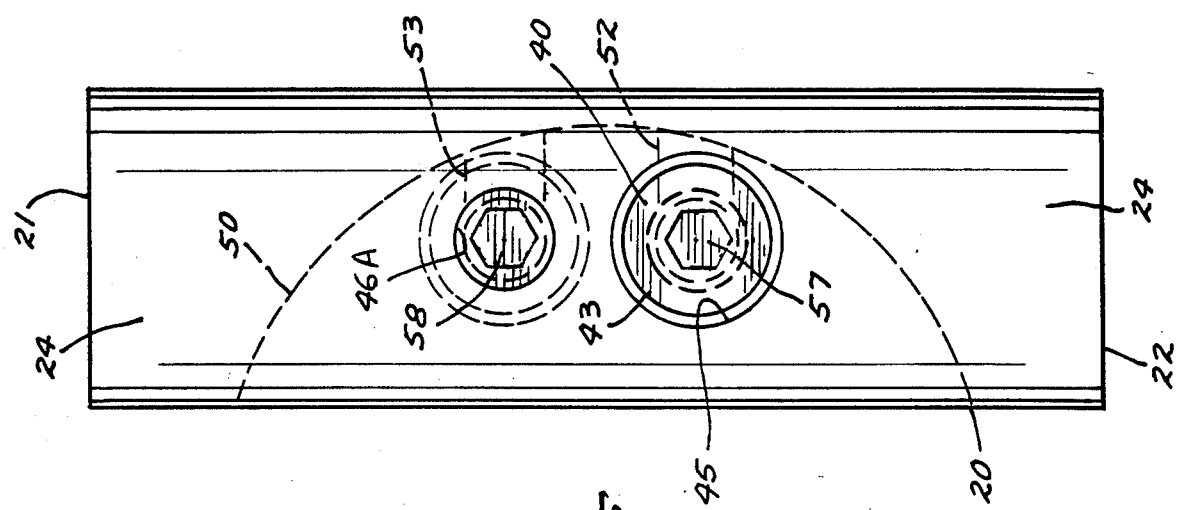
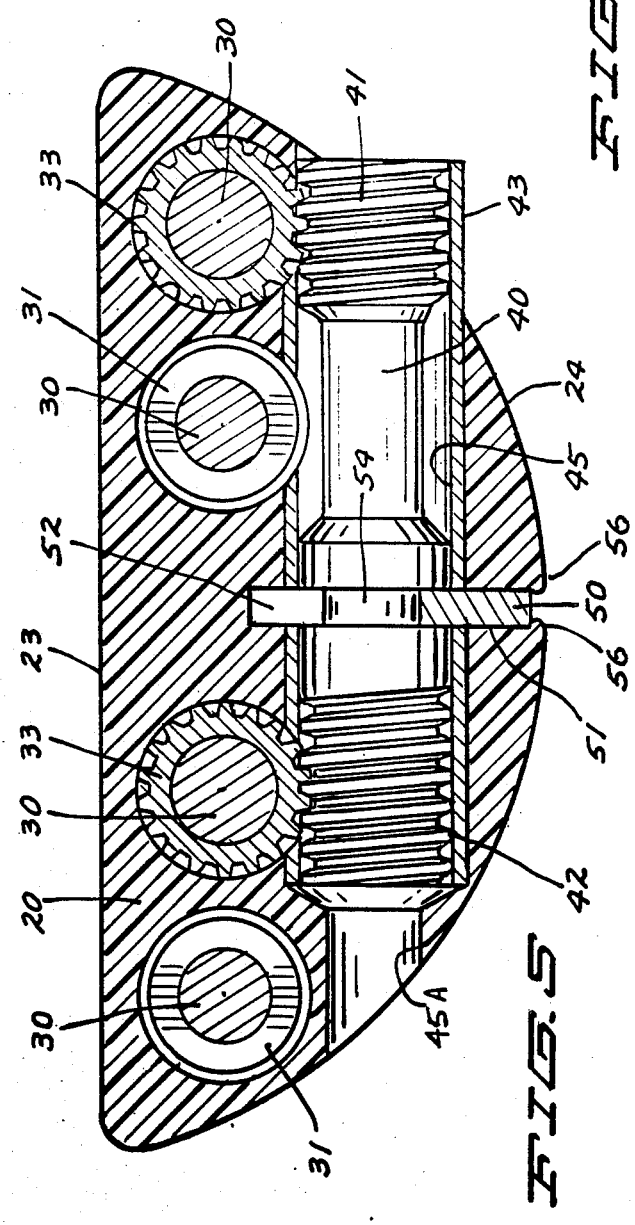
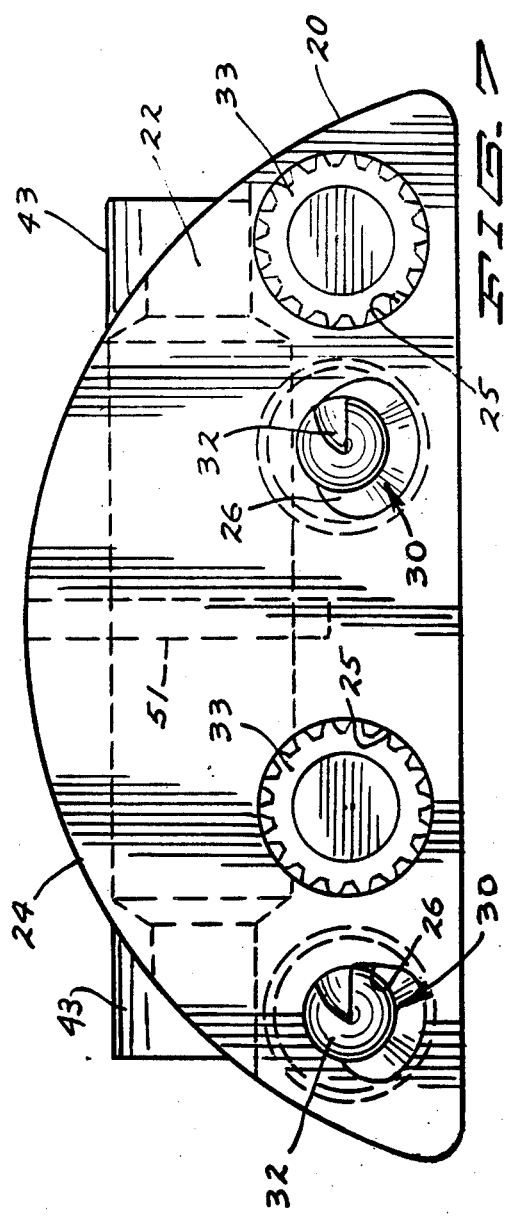

ANTERIOR SPINAL IMPLANT

BACKGROUND OF THE INVENTION

1. Field of the Invention

The present invention relates to an implantable insert for replacement fo anterior portions of vertabrae.

2. Description of the Prior Art

Anterior spine braces have been used for spinal column support. Such devices are sold by Zimmer, Inc. of Warsaw, Ind. USA, and are disclosed in the publication "Instrumentation for the Anterior Spine" by Harry K. Dunn, M.D. The brace comprises a bridge member that will span an injured vertebra or the void left, if it has been removed, by attaching supports above and below the damaged vertebra on the exterior of the spine. The supports are then screwed into place and are connected by one or more rods which provide compression carrying ability across the injured vertebra. A similar device is used for treatment of congenital scoliosis, and in each instance the brace that is utilized protrudes to the exterior of the spinal column. While the system is useful for treating certain problems, its installation and adjustment are difficult and it intrudes into the body cavity.

There have been various prostheses for spinal corrections and the like described in the patented art as well. A general type of brace which clamps onto the spinal column for correction of scoliosis is shown in U.S. Pat. No. 4,361,141. The patent discloses use of exterior rods which provide traction for the spinal column for straightening the spine. This device is not for replacement or support of an individual vertebra. A similar spinal column prosthesis utilizing exterior clamping mechanisms is shown in U.S. Pat. No. 4,085,744.

U.S. Pat. No. 4,422,451 also shows a spinal compression and distraction device which includes a type of a clip that hooks onto the spinal column and which will receive a rod for applying either distraction or compression loads to the spinal column, depending on the problem being treated.

U.S. Pat. No. 4,433,677 illustrates a device that is implantable, and forms a splint that is anchored in the pelvis and has upwardly extending rods that engage the spinal column to provide a spinal column support. This type of device, again, is on the exterior of the spine, which causes problems for the patient.

U.S. Pat. No. 3,867,728 shows a spinal repair prosthesis which replaces an injured disc between vertebrae. It has no fastening, other than normal ingrowth of tissue after it has been inserted in between two vertebrae.

A similar disc prosthesis is shown in U.S. Pat. No. 4,349,921 which again is for replacing a disc between two vertebrae and which is made so that it will conform to adjacent vertebral surfaces.

SUMMARY OF THE INVENTION

The present invention relates to a directly implanted prosthetic insert for replacing a vertebral body that is damaged. The insert will maintain the height of the anterior spinal column, thus preventing defomities from occurring. The device is implanted into the spinal column after the affected anterior vertebral body has been removed, or at least resected sufficiently to provide clearance for the implanted insert body. The insert body houses screw members that are initially retracted completely within the insert body. The height of the insert body is selected to be compatible with the height of the anterior vertebral portion that it is to replace. The insert body is then slipped into place between adjacent upper and lower vertebrae and the screws actuated to thread the body into adjacent bone. There are no substantial protrusions into the body cavity of the patient which reduces irritation to adjacent tissue.

The first function of the insert body is to serve as a spacer for the maintenance of spinal alignment following removal of a portion of diseased spine. Its second function is to provide an element of rigid internal fixation so that body healing can take place across the segment spanned by the insert body.

The insert body is provided with a drive mechanism which will drive the retaining screws upon rotation of the drive mechanism. This drive mechanism comprises drive gears having a drive connection accessible from the exterior of the insert body after the insert has been placed into the void. A drive wrench is coupled to the drive connection and moved to rotate the drive gears, which will rotate the self-tapping, bone penetrating retaining screws so that they will be driven outwardly from the opposite end surfaces of the implanted insert body.

In the form shown, two drives for the screws are utilized. The first drive member controls the movement of two screws from one end of the insert body, while the second drive controls two screws that emerge from the other end of the insert body. In the procedure, normally the screws that emerge from the top of the implanted insert body are first driven into the upwardly adjacent vertebra first, and then the screws from the lower or inferior border of the insert body are driven to enter the vertebral body below the insert body.

The implanted insert is of a size so that it does not protrude outwardly from the anterior margins of the anterior vertebral column and only slight lateral protrusion is permitted. The body has a semi-circular cross section that closely approximates the cross section of the anterior vertabrae. Slight protrusions to the lateral sides of the insert body can be tolerated but no protrusions toward the interior of the patient's body cavity are present.

The size of the insert body is particularly important at locations such as the fifth lumbar vertebral level, since in this region overlying iliac vessels make a bulky implant difficult, if not impossible to apply.

The insert body is made of surgical grade nylon, in its preferred form, and the bone screws and drives are made of surgical grade stainless steel. The height of the insert body, that is, its dimension in direction along the spinal column, can be varied in standard lengths for different size spinal columns, to accommodate patients having different bone structure, and also for different locations in the spinal column.

The implantation of the insert body is simplified in that it requires smaller access openings through the patient's body, and once in place, and secured, provides rigidity that is limited only by the bone structure of the adjacent vertebrae to which the insert body is affixed. Because the insert body is rigidly held in place and does not protrude beyond the margins of the spinal column, bony healing can take place rather rapidly and there are no protrusions which would tend to irritate adjacent tissue. The implant procedures do not injure the spinal cord, but the adjacent spinal or vertabral discs are removed so that the insert body will be held with screws anchored directly into the bone of the next adjacent vertebrae with the implant body and surface contiguous to the bone surfaces.

BRIEF DESCRIPTION OF THE DRAWINGS

FIG. 5 is a sectional view taken as on line 5—5 in FIG. 4; and

FIG. 6 is a side elevational view of the insert body of FIG. 4; and

FIG. 7 is a bottom plan view of the insert body of FIG. 4.

DETAILED DESCRIPTION OF THE PREFERRED EMBODIMENTS

An anterior spinal implant prosthetic insert illustrated generally at 10 is made to replace an anterior portion of a vertebra in a spinal column indicated generally at 11. The implant 10 is positioned, as shown, on the anterior of the spinal column between an upper vertebra indicated at 12, and a lower or inferior vertebra indicated at 13.

The spinal column includes posterior vertabrae portions indicated at 14, which define a neural canal 15 in which the spinal cord is carried.

The insert 10 is used for complete replacement of a removed anterial vertebra, or it can be inserted after the vertebra has been resected to provide clearance for the insert body.

Figure 1:
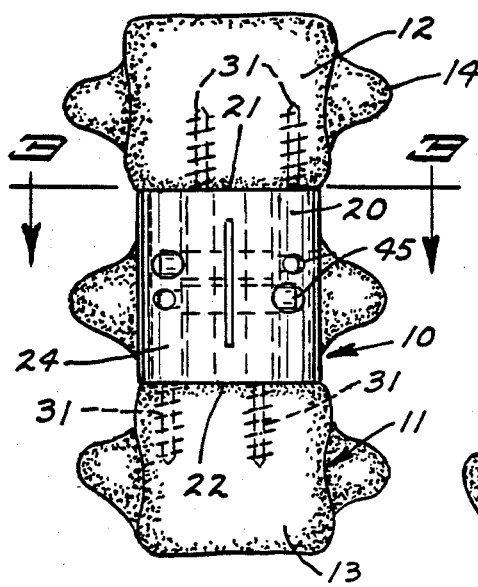
FIG. 1 is a part schematic representation of a spinal column having an implanted vertebra prosthetic insert made according to the present invention installed therein.
Figure 2:
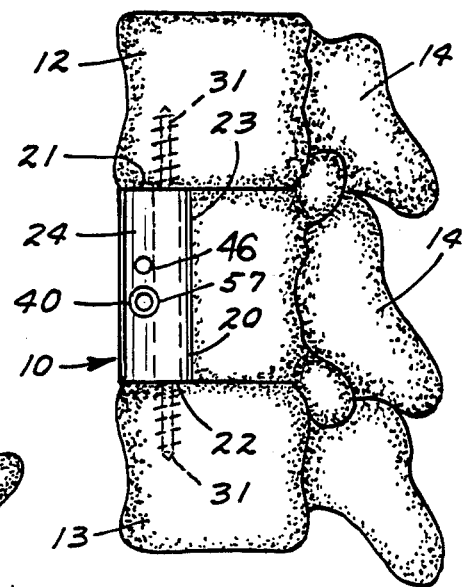
FIG. 2 is a side elevational view of the device of FIG. 1.
Figure 3:
FIG. 3 is a sectional view of a modified implanted insert taken on line 3—3 in FIG. 1.

The insert 10 comprises an insert body or housing 20 which has an upper end surface 21, and a lower end surface 22, a generally planar posterior surface 23 and a part cylindrical outer or anterior surface 24, which faces toward the body cavity of a patient. As shown in FIG. 3, a support neck or column 19 can be found at the rear of the insert and extend the full length of the body 20 between surfaces 21 and 22. The insert body thus has a part circular cross section.

The insert body 20 is made of a suitable surgical grade plastic, such as surgical grade nylon, and is provided with screws for securing the insert body to the next adjacent vertebrae 12 and 13, respectively. The vertical height of the insert body 20 is selected to abut against the adjacent bony surfaces adjacent the end surfaces 21 and 22 of the vertebrae 12 and 13, after the discs normally present between vertebrae are removed. Thus, the length of the insert body can be selected to suit existing circumstances, and generally speaking standard sizes ranging in increments of approximately 5 millimeters in length have been found to be satisfactory. Typically, the insert body would have a transverse dimension of about 3.5 cm and lengths of 35 to 50 mm. The insert body 20 as shown is provided with longitudinally extending bores (extending between the top and bottom surfaces) for receiving screws which will be screwed into the adjacent vertebrae. In the form shown, there are two bores 25, which house screws 30 that will extend from the upper surface 21 after the insert body has been put into place, and there are two bores 26 which house screws 30 which will extend from the lower surface 22 of the insert body 20.

The bores 25 and 26 are identically constructed, but are oriented in opposite directions. Each of the bores has a cylindrical mounting portion 25A and 26A, respectively, and an interior threaded end portion 25B and 26B, respectively. The threaded end portions have helical threads 25C and 26C threadably receiving identical surgical screws 30. The screws 30 have threaded portions indicated at 31 that mate with the threads 25C and 26C, respectively. The screws 30 have self tapping ends 32 of conventional design so that as each screw is rotated and moved outwardly from the body, it will tend to tap itself into any body that penetrates. In particular, these screws tap into cancellous bone.

The opposite ends of the screws 30 are provided with a worm wheel or gear section 33 that is rotatably mounted in the cylindrical portions of the respective bone 25 or 26. A thrust washer 34 is provided at the inner end of the gears 33, on each of the screws and the thrust washer will, when the respective screw is fully extended along its longitudinal axis in the respective direction, abut against a shoulder surface 35 formed between the bores 25A and the bore 25B, and bores 26A and 26B, respectively. The thrust washers 35 are spaced from the inner ends of the threaded portions 31 of the screws.

The worm gears 33 on the screws 30 are driven by drive gears called worms. The screws 30 that are mounted in the bores 25 are driven by a first worm drive shaft 40 that has a first worm section 41, and a second worm section 42 drivably mounted thereon. The shaft 40 and worms 41 and 42 are mounted inside a tubular housing 43 that in turn is positioned in a cross bore 45 formed in the insert body 20 and which has a longitudinal axis generally perpendicular to the rotational axes of the screws 30.

A second drive shaft 40 is mounted in a housing 43 which is positioned in a bore 46. Bore 46 is positioned above the bore 45, and parallel to it, and the second worm drive shaft 40 is identically constructed to the first worm drive shaft 40 except that it is turned end for end, and the worm sections 41 and 42 of the second worm drive shaft engage the worm gears 33 on the screws 30 that are mounted in the bores 26.

It should be noted that the housing tube 43 for the respective worm shaft and worm gears is closely fitted into a larger diameter portion of bores 45 and 46. The opposite ends of the bores 45 and 46 indicated at 45A, 46A are of smaller diameter.

The housing tubes 43 are also made in two sections, and a thrust plate 50 is inserted into a provided slot shown at 51 centered on the insert body 20. The thrust plate 50 is perpendicular to the axes of the tubes 43. The thrust plate 50 is slotted as shown in dotted lines at 52 and 53, to receive a reduced neck section 54 of the shaft 40, to hold the worm shafts from axial movement as they are threaded to drive the worm gears or wheels 33 on screws 30. The thrust plate 50 can be held in place by upsetting the outer edges 56 of the slot 51 as shown.

The opposite ends of the worm shaft 40 are provided with internal polygonal openings indicated at 57 and 58, respectively, to receive suitable drive key wrenches, (such as Allen wrenches for a hex-shaped socket) for rotating the worm shafts from the exterior of the insert body 20.

It can be seen that the worms 40 and 41 engage the gears 33 of respective screws in the two bores that the particular worm shaft 40 controls, and the tube 43 is formed with openings to permit the gears 33 to extend into the housing tube 43 to engage the worm gears. Each worm shaft is recessed to provide clearance for the gear 33 of the other set of screws which is between the two screws that are driven by that shaft. Also, each shaft 40 stops short of the end screw from the other set, as shown typically in FIGS. 5 and 7.

Figure 4:
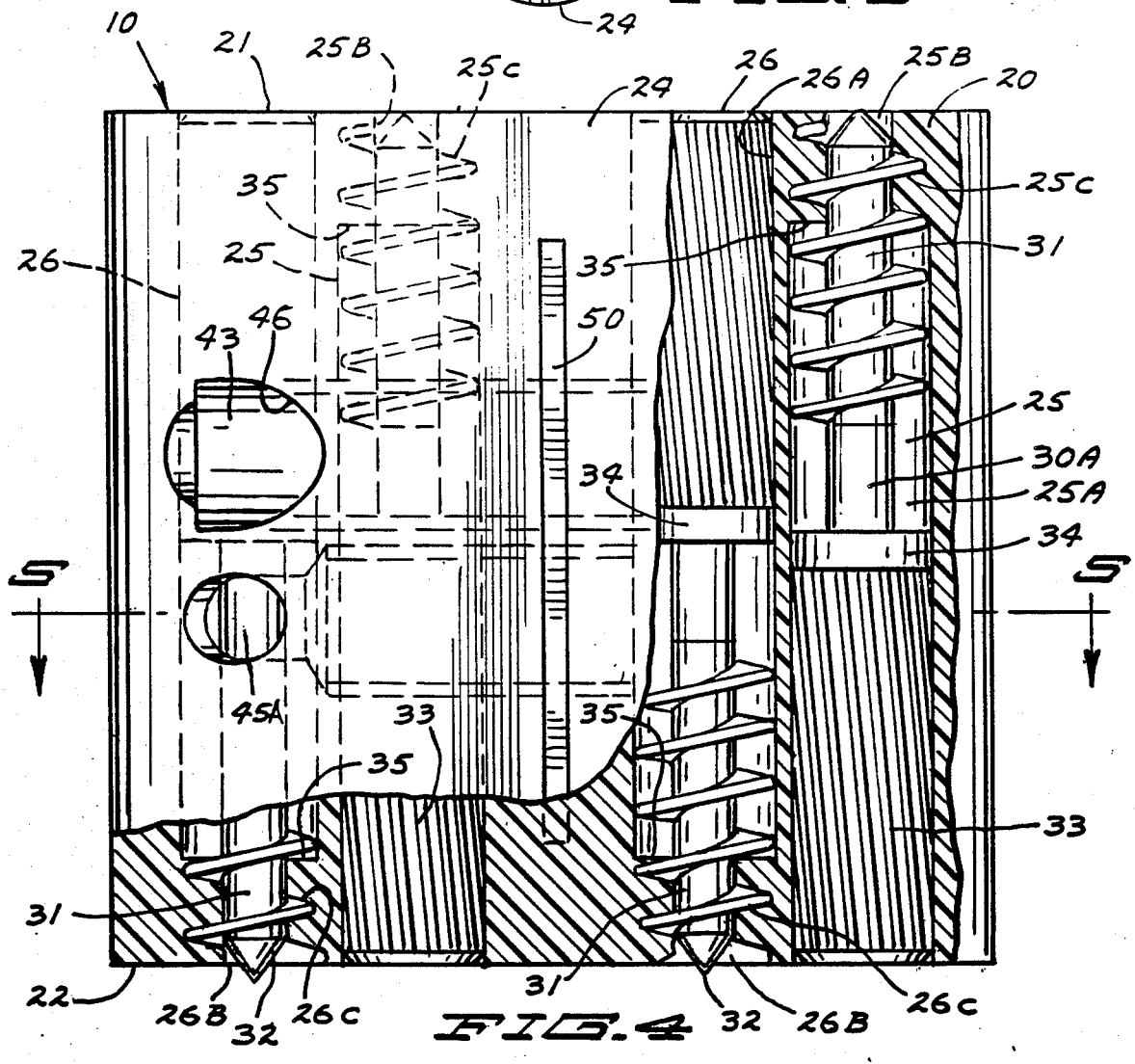
FIG. 4 is an enlarged front elevational view of the prosthetic insert body made according to the present invention.

When the screws 30 and drive worm shafts 40 are assembled into the insert body 20, the screws 30 are initially in retracted position as shown in FIG. 4. The screws 30 do not protrude from the respective end surfaces of the insert body 20.

The injured or diseased vertebra to be replaced with the implanted insert is made accessible through standard surgical techniques generally as described in the publication "Instrumentation for the Anterior Spine" by Harold K. Dunn, M.D., published by Zimmer, Inc. The anterior vertabra portion to be replaced is removed, and the insert body 20, with the screws 30 fully retracted within the body, so that the surfaces 21 and 22 are smooth, is placed into the void left by the removal of the diseased vertebral segment. The insert body 20 is positioned properly in lateral directions. The insert body is formed so that it is completely within the margins of the spinal column and while the housing tubes 43 protrude slightly laterally from the part-cylindrical surface, they do not cause any problems. A drive wrench is inserted into one of the sockets 57 or 58 for the first worm shaft 40 to rotate the associated screws 30, for example the screws in the bores 25. The drive causes the screws 30 to be screwed out of the housing to protrude from the surface 21 into the next adjacent upper vertebra. As the screws 30 are rotated they will be threaded outwardly by the threads 25C and the threads 31, and the self tapping end 32 will engage the bone and the screw will tap into the vertebral bone immediately above the implanted insert body. The screws 30 can be driven until they are fully extended and the thrust washer 34 contacts the shoulder 35. In this position, the screw shanks 30A are positioned in the interior threads of the bores 25 and 26 and the screw threads clear the thread sections 25C and 26C. Further rotation of the screws then causes the adjacent vertabrae at each end of the insert body to be tightened against the end surfaces of the insert body to a desired degree.

Then, the second worm shaft 40 is driven in the same manner, using a suitable drive wrench and the sockets 57 or 58, depending on which end is most accessible, until the second set of screws 30 that are in the bores 26 are fully extended and tapped into the next adjacent lower vertebra to firmly immobilize the implanted insert body relative to the two adjacent vertebra. The adjacent vertrabra can be compressed against the ends of the insert body by the action of the screws. The implant procedure is then completed.

The rigidity imparted to the spinal column will vary according to the status of the bone of the adjacent portions of the spinal column, and bone integrity, rather than failure of the implant insert body itself is the limiting factor. Since no substantial residual material is left outside of the margins of the anterior vertebral column, there is no interference or irritation of tissue or vessels adjacent the spinal column. The implanted insert body serves as a spacer for the maintenance of spinal alignment following the removal of a portion of the diseased spine, and also provides an element of rigid internal fixation so that bony healing can take place across the segments spanned by the implant.

A single drive worm shaft may be used for driving the screws out of the top and bottom of the implant simultaneously, but this requires more torque or power for driving, and an arrangement to have opposite direction of rotation of the two sets of screws. The use of the separate drives for the two sets of two screws each requires less drive torque, so there is less likelihood of causing misalignment or misplacement of the implant due to operation of the drive wrench and the worm shafts.

The worm shafts, the housing tubes 43, and the thrust plate 50 can be made of surgical grade stainless steel. The nylon insert body provides for a low friction rotation of the screws as they are screwed into the bones of adjacent vertebrae.

It also should be noted that the insert body can be made in a length that will span a void left by the removal of two adjacent vertebrae, if desired.

The modified form of insert body shown in FIG. 3 is useful when a greater portion of the injured vertebrae has to be removed. The portion 19 shown provides support across a larger area. The immobilizing fasteners and drives therefore are the same as the detailed showing in FIGS. 4 through 7.

Although the present invention has been described with reference to preferred embodiments, workers skilled in the art will recognize that changes may be made in form and detail without departing from the spirit and scope of the invention.

What is claimed is:

1. An implantable prosthesis for replacement of a vertebral bone portion comprising;
   a body of size to fit within a void left by removal of a vertebral portion from a spinal column of a patient, said body having a first axis positioned to generally align with the direction of extension of a spinal column in which the body is to be inserted and having generally planar end surfaces transverse to the axis at opposite ends of the body;
   at least two bore means in said body, at least one bore means extending in each direction of said axis;
   a separate self tapping bone screw in each bore means, said screws being threadably engaged with a portion of the bore means so that each screw will be selectively extended or retracted relative to one of the end surfaces of said body upon rotation of such screw; and
   drive means for rotation of each of said screws in its respective bore means, said drive means being positioned to be accessible from a lateral side of the body when the body is placed into a void between two adjacent vertebrae sections, said drive means being actuable to thread the screws through the respective bore means to tap into the bone adjacent opposite end surfaces, to secure the body in place.

2. The apparatus as specified in claim 1 wherein said drive means comprises a worm shaft, each of said screws having a worm gear section, said worm shaft having a worm portion positioned so that upon rotation of the worm shaft, the worm gear of at least one screw will be driven to rotate the screw.

3. The apparatus as specified in claim 1 wherein there are four bore means in said body, two of said bore means having threaded portions carrying screws which upon rotation thereof will be extended from a first end of said body, and two of said bore means having threaded portions carrying screws which upon rotation thereof will be extended from the second end of said body.

4. The apparatus as specified in claim wherein said body has a part cylindrical outer surface extending between the end surfaces and generated about an axis generally parallel to the body axis, and wherein said worm shaft is positioned in a cross bore that intersects the part cylindrical outer surface of said body, so that the worm shaft is accessible from a lateral side of said body.

5. An implantable prosthesis for replacement of a vertebral bone portion comprising:
   a body of size to fit within a void left by removal of a vertebral portion from a spinal column of a patient, said body having a first axis positioned to generally align with the direction of extension of a spinal column in which the body is to be inserted and having end surfaces extending transverse to the axis;
   bore means in said body extending in direction of said axis;
   a separate screw in each bore means, said screws being threadably engaged with a portion of the bore means so that each screw will be selectively extended or retracted relative to one of the end surfaces of said body upon rotation of such screw; and
   drive means for rotation of each of said screws in its respective bore means comprising drive shaft means rotatable from the exterior of said body when the body is in position in a void in a spinal column, and cooperating gear means between said drive shaft means and said screws for selectively rotating each screw to extend or retract such screw as the drive shaft means is rotated.

6. The apparatus as specified in claim 5 wherein said body has a part cylindrical outer surface extending between the end surfaces and generated about an axis parallel to the body axis, the part-cylindrical surface being within the marginal portions of the spinal column in which the body is implanted.

7. An implantable prosthesis for replacement of a vertebral bone portion comprising:
   a body of size to fit within a void left by removal of a vertebral portion from a spinal column of a patient, said body having a first axis positioned to generally align with the direction of extension of a spinal column in which the body is to be inserted and having first and second spaced apart end surfaces transverse to the axis, said body having a predetermined length between the end surfaces;
   bore means in said body extending in direction of said axis, said bore means including first bore means threaded adjacent the first end surface of said body, and second bore means threaded adjacent the second end surface of said body;
   a separate screw rotatably mounted in each bore means, said screws being threadably engaged with the threaded portion of the respective bore means so that each screw will be selectively extended or retracted relative to one of the end surfaces of said body upon rotation of such separate screw; and
   drive means positioned to be accessible from a lateral side of said body when the body is placed into a void between two adjacent vertebrae sections, said drive means being rotatable for rotating said screws to cause said screws to be threaded to extend from the respective end surfaces, said screws including self tapping ends for tapping a screw path into adjacent portions of a spinal column in which the insert is placed as the screws are rotated.

8. The apparatus as specified in claim 7 wherein said body is made of a suitable surgical grade plastic, and said screw means comprise stainless steel self tapping bone screws.

9. The apparatus as specified in claim 7 wherein said drive means comprises a set of cross bores transversely positioned with respect to said bore means, a separate sleeve mounted in each of said cross bores, a separate drive shaft having a first gear thereon mounted in each sleeve, means on each of the screws comprising a second gear engaging one of said first gears, whereby rotation of said drive shafts causes a drive connection through said first and second gears to rotate the respective screw in a predetermined direction.

10. An implantable prosthesis device for replacement of an anterior vertebra comprising:
    an insert body having a first axis, said body having first and second end surfaces spaced apart along said first axis, and extending generally perpendicular to said first axis, and said body having a part cylindrical surface generated about an axis parallel to said first axis and a base surface comprising a chordal plane surface relative to said part cylindrical surface;
    a plurality of bores in said body extending generally parallel to said first axis, a first of said bores having a threaded internal portion adjacent the first end surface, and a second of said bores having an internally threaded portion adjacent the second end surface,
    a first screw mounted in said first bore and having a self tapping end and being threadably engaged with the internal threaded portion of said first bore;
    a second screw having a self tapping end and being threadably engaged with the internally threaded portion of said second bore adjacent said second end surface, said screws having a length to permit them to be completely within the body when they are in a retracted position, respectively; and
    drive means for individually driving each of said first and said second screws comprising drive shaft means extending generally transverse to the first axis, and being accessible through said part cylindrical surface, said drive means including right angle drive means between the drive shaft means and the screws to permit rotation of the screws upon rotation of the drive shaft means to tend to thread said screws from their retracted position outwardly from the respective end surface of the body.

11. The apparatus as specified in claim 10 wherein said drive means comprises worm gear drive means cooperating between the drive shaft means and each of said screws.

12. The apparatus as specified in claim 11 wherein the drive shaft means comprises two drive shafts, one drive shaft for driving each of said screws.

13. The apparatus as specified in claim 12 wherein said bores have internal shoulders, and the screws each having a thrust collar spaced inwardly from threaded portions of the screws, and said thrust collar bearing against the internal shoulders to limit the extension of said screws.

* * * * *

UNITED STATES PATENT AND TRADEMARK OFFICE
CERTIFICATE OF CORRECTION

PATENT NO. : 4,636,217

DATED : January 13, 1987

INVENTOR(S) : James W. Ogilvie et al.

It is certified that error appears in the above-identified patent and that said Letters Patent is hereby corrected as shown below:

Column 7, line 4, after "Claim", delete "1" and insert --2--.

Signed and Sealed this

First Day of September, 1987

*Attest:*

DONALD J. QUIGG

*Attesting Officer*    *Commissioner of Patents and Trademarks*